(12) United States Patent
Ban (10) Patent No.: US 9,717,620 B2
(45) Date of Patent: Aug. 1, 2017

(54) FOOTWEAR

(71) Applicant: NCC CO., LTD., Aichi (JP)

(72) Inventor: Toshiki Ban, Aichi (JP)

(73) Assignee: NCC CO., LTD., Aichi (JP)

( * ) Notice: Subject to any disclaimer, the term of this patent is extended or adjusted under 35 U.S.C. 154(b) by 0 days.

(21) Appl. No.: 14/836,930

(22) Filed: Aug. 26, 2015

(65) Prior Publication Data

US 2016/0081837 A1  Mar. 24, 2016

Related U.S. Application Data

(63) Continuation of application No. PCT/JP2014/067733, filed on Jul. 3, 2014.

(51) Int. Cl.
| | | |
|---|---|---|
| *A43B 7/14* | (2006.01) | |
| *A61F 5/01* | (2006.01) | |
| *A43B 3/10* | (2006.01) | |
| *A43B 3/12* | (2006.01) | |

(52) U.S. Cl.
CPC ............ *A61F 5/0111* (2013.01); *A43B 3/108* (2013.01); *A43B 3/12* (2013.01); *A43B 3/128* (2013.01); *A43B 7/149* (2013.01); *A43B 7/1415* (2013.01); *A43B 7/1445* (2013.01); *A43B 7/1485* (2013.01)

(58) Field of Classification Search
CPC ... A43B 7/1415; A43B 7/1445; A43B 7/1485; A43B 7/149; A43B 3/128; A43B 3/108; A61F 5/04; A61F 5/042; A61F 5/01; A61F 5/14
USPC .................................. 36/140, 145, 180, 182
See application file for complete search history.

(56) References Cited

U.S. PATENT DOCUMENTS

| | | | | |
|---|---|---|---|---|
| 1,676,355 A | * | 7/1928 | Saperston ............ | A43B 7/1415 36/146 |
| 1,850,977 A | * | 3/1932 | Musebeck ................ | A43B 7/14 36/145 |
| 1,992,081 A | * | 2/1935 | Madinger .............. | A43B 7/142 36/178 |
| 2,310,824 A | * | 2/1943 | Wyant .................... | A43B 7/142 36/145 |

(Continued)

FOREIGN PATENT DOCUMENTS

| | | |
|---|---|---|
| FR | 2844995 A1 | 4/2004 |
| JP | 8-131207 A | 5/1996 |

(Continued)

OTHER PUBLICATIONS

Translation of WO/2008/146376.*
International Search Report PCT/JP2014/067733 dated Sep. 22, 2014 with English translation.

*Primary Examiner* — Ted Kavanaugh
(74) *Attorney, Agent, or Firm* — McDermott Will & Emery LLP (57) ABSTRACT

Provided is footwear whereby it is possible to desirably carry out correction and stretching of a transverse arch of a foot. A transverse arch pressure part which protrudes such that a cross-section in the width direction is an arc shape is formed between portions in a foot contact surface of an article of footwear directly below the ball of the large toe and the ball of the little toe, and a pair of runners which do not support the ball of the large toe or the ball of the little toe are formed in the foot contact surface directly below the ball of the large toe and the ball of the little toe.

4 Claims, 8 Drawing Sheets

(56) References Cited

U.S. PATENT DOCUMENTS

| | | | | | |
|---|---|---|---|---|---|
| 2,411,901 | A | * | 12/1946 | Silver | A43B 7/1415 36/145 |
| 2,591,378 | A | * | 4/1952 | Scholl | A43B 7/1445 602/30 |
| 4,250,886 | A | * | 2/1981 | Riso | A43B 7/14 36/180 |
| 4,266,350 | A | * | 5/1981 | Laux | A43B 7/144 36/3 B |
| 4,967,750 | A | * | 11/1990 | Cherniak | A43C 11/1493 36/11.5 |

FOREIGN PATENT DOCUMENTS

| | | |
|---|---|---|
| JP | 2006-187545 A | 7/2006 |
| JP | 2009-017938 A | 1/2009 |
| JP | 2012-187374 A | 10/2012 |
| WO | 2008/146376 A1 | 12/2008 |

* cited by examiner

FOOTWEAR

RELATED APPLICATIONS

This application is a Continuation Application of International Application No. PCT/JP2014/067733, filed Jul. 3, 2014, which claims priority to Japanese Application No. 2013-232048, filed Nov. 8, 2013. The subject matter of each is incorporated herein by reference in entirety.

FIELD OF THE INVENTION

The present invention relates to footwear used for stretching and correcting feet.

BACKGROUND ART

Human feet support the body at three positions, thenar eminences (joints of big toes), hypothenar eminences (joints of little toes), and heels while the human stands up straight. The human foot has three arch structures bridged across these positions. The arch structures are consisted of muscles and ligaments. These arch structures serve as a cushion to absorb an impact applied to the three positions. Specifically, the three arch structures are formed of a medial longitudinal arch, a lateral longitudinal arch, and a transverse arch. The medial longitudinal arch is bridged across the thenar eminence and the heel and forms a plantar arch. The lateral longitudinal arch is bridged across the hypothenar eminence and the heel. The transverse arch is bridged across the thenar eminence and the hypothenar eminence.

Nowadays, increasingly more people suffer from fallen transverse arch or the arch warped in the opposite direction (downward) due to wearing high-heeled footwear or similar footwear, which causes an excessive load to be applied to the toes. Thus, the person whose shape of the transverse arch has collapsed cannot sufficiently absorb an impact applied to the feet and therefore easily gets tired. Additionally, the person is likely to develop a hallux valgus, a callus, a clavus, or a similar symptom. To prevent the problem caused by collapsing of the transverse arch, there has been proposed footwear and a sole insert whose foot contact surfaces are bulged into the shape of the transverse arch to support the transverse arch during wearing (see Patent Literatures 1 to 3).

CITATION LIST

Patent Literature

Patent Literature 1: Japanese Unexamined Patent Application Publication No. 2009-17938
Patent Literature 2: WO 2008/146376
Patent Literature 3: Japanese Unexamined Patent Application Publication No. 2012-187374

SUMMARY OF THE INVENTION

Problem to be Solved by the Invention

Figure 8:
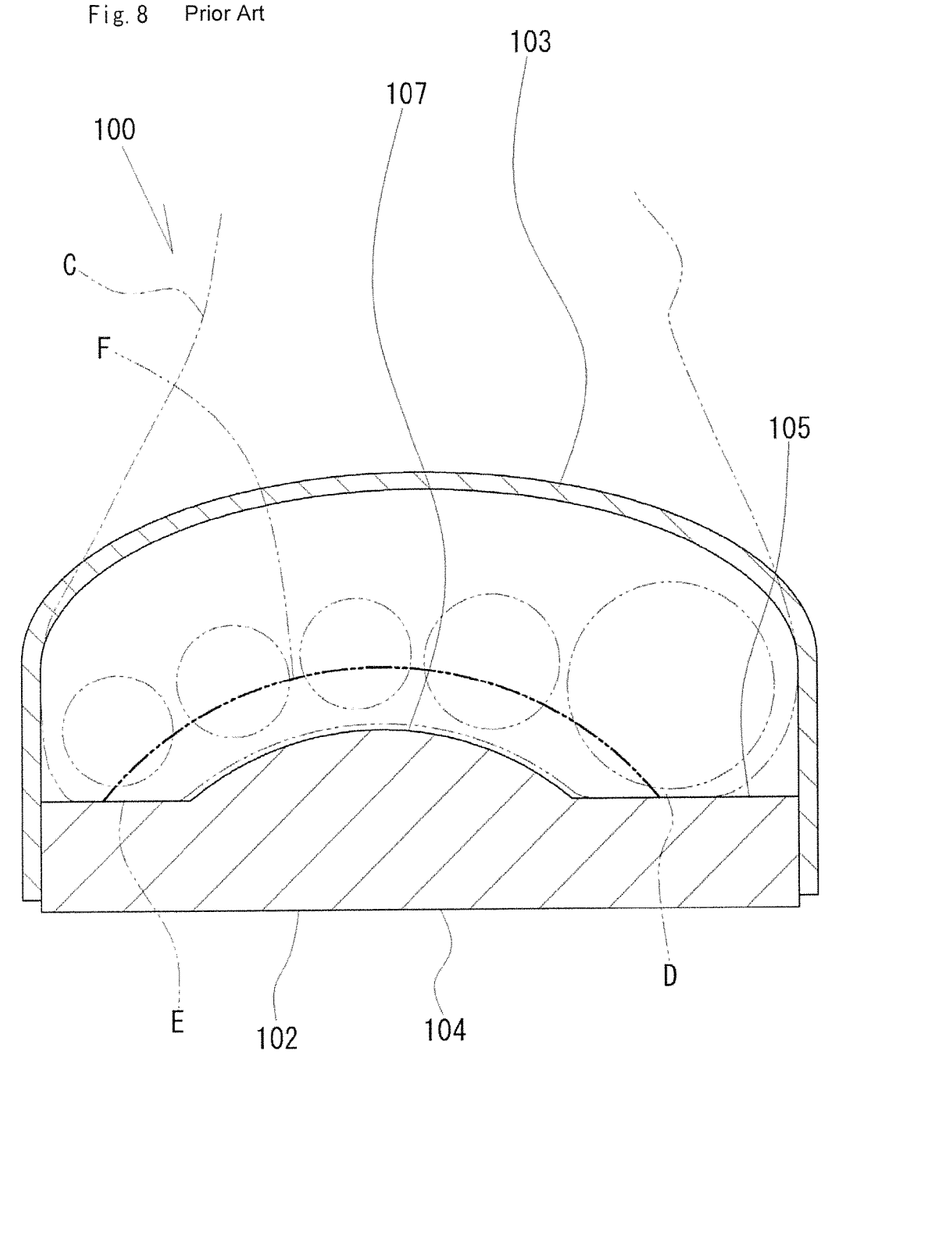
FIG. 8 is a cross-sectional view of conventional footwear 100.

Conventional footwear 100 described in the Patent Literatures, as illustrated in FIG. 8, supports a transverse arch F from below during wearing to reduce a load applied to the transverse arch F, thus ensuring preventing the collapse of the transverse arch F. Reference numeral 102 in FIG. 8 denotes a footwear body. Reference numeral 103 denotes an instep cover that covers an instep of a foot C. Reference numeral 104 denotes a ground contact surface in contact with the ground. Reference numeral 105 denotes a foot contact surface in contact with a sole. However, such footwear 100 supports the transverse arch F from below with a bulge part 107 of the foot contact surface 105 in a state where the foot contact surface 105 supports a thenar eminence D and a hypothenar eminence E of the foot C. Accordingly, the footwear 100 does not strongly pressurize the site forming the transverse arch F from below. In view of this, the effect of the footwear 100 is to just prevent the collapse of the transverse arch F during wearing this footwear 100. Even if this footwear 100 is worn, the shape of the transverse arch F collapsed by other causes cannot be recovered or corrected.

The present invention attempts to solve the problem, and the object is to provide footwear with which the transverse arches of the feet can be preferably corrected and stretched.

Means for Solving Problem

The present invention includes a transverse arch pressurizing portion and a pair of escaping portions. The transverse arch pressurizing portion is formed at a part immediately below between a thenar eminence and a hypothenar eminence on a foot contact surface. A widthwise cross-section of the transverse arch pressurizing portion bulges arcwise. The pair of escaping portions are formed at parts immediately below a thenar eminence and a hypothenar eminence on a foot contact surface. The escaping portions do not support a thenar eminence and a hypothenar eminence. The escaping portions are constituted such that a foot contact surface does not support a thenar eminence and a hypothenar eminence.

During wearing the footwear of the present invention, the foot contact surface does not support the thenar eminence and the hypothenar eminence. Accordingly, a load usually supported by the thenar eminence and the hypothenar eminence is not applied to the thenar eminence and the hypothenar eminence. The transverse arch pressurizing portion applies a strong load to a site forming the transverse arch (hereinafter referred to as a transverse arch formation site) between the thenar eminence and the hypothenar eminence. Thus, according to the footwear of the present invention, the transverse arch pressurizing portion can strongly pressurize the transverse arch formation site of the foot from below. Accordingly, the bulge shape of the transverse arch pressurizing portion with arcwise cross-section ensures correcting the shape of distorted transverse arch. Additionally, this stretches the muscles forming the transverse arch, allowing recovery of fatigue muscle. Especially, the footwear of the present invention strongly pressurizes the transverse arch formation site, which is advantageous in that a sufficient effect can be obtained by just wearing the footwear for several minutes to several tens of minutes, eliminating the need for wearing for a long time.

As the specific constitution of the escaping portion according to the present invention, the following constitution is proposed. At least one of the escaping portions is formed lower than the transverse arch pressurizing portion to prevent the foot contact surface from being brought in contact with a thenar eminence or a hypothenar eminence. As another constitution, the following constitution is proposed. The at least one escaping portion is formed by eliminating a part immediately below a thenar eminence or a hypothenar eminence to prevent a foot contact surface from being brought in contact with a thenar eminence or a hypothenar eminence.

With this constitution, the thenar eminence and the hypothenar eminence are not in contact with the foot contact surface. This allows almost all loads, which are usually supported by the thenar eminence and the hypothenar eminence, to be applied to the transverse arch formation site.

As another constitution, the following constitution is proposed. The at least one escaping portion is constituted of an inclined contacting portion and a non-contacting portion. The inclined contacting portion is inclined downward from a side edge of the transverse arch pressurizing portion to an outer side at an angle of 45° or more, and is in contact with an inner portion of a thenar eminence or a hypothenar eminence. The non-contacting portion is formed on an outer side of the inclined contacting portion, and is not in contact with a thenar eminence or a hypothenar eminence.

With this constitution, the inner portion of the thenar eminence or the hypothenar eminence is in contact with the foot contact surface at the inclined contacting portion. However, even if the thenar eminence and the hypothenar eminence are in contact with the inclined contacting portion of steep incline, the thenar eminence and the hypothenar eminence cannot support the body. Accordingly, even with the constitution, the strong load can be applied to the transverse arch pressurizing portion. The non-contacting portion may be formed at a low position so as not to be in contact with the thenar eminence and the hypothenar eminence. The non-contacting portion may also be eliminated including the ground contact surface.

The present invention proposes the following. The footwear is sandal type footwear including a footwear body and an instep cover. The footwear body forms a foot contact surface and a ground contact surface. The instep cover covers an instep of foot. The instep cover includes a pair of instep cover pieces and coupling means. The respective instep cover pieces are fixedly secured to both lateral portions of a footwear body. The coupling means mutually couples these pair of instep cover pieces to be removable/mountable. The instep cover is changeable between a covering state and an open state. The covering state couples a pair of instep cover pieces with coupling means to cover an instep of foot. The open state mutually separates a pair of instep cover pieces to open the pair of instep cover pieces to an outside.

With this constitution, setting the instep cover to the open state to open the top of the foot contact surface allows the transverse arch formation site to be accurately and easily placed on the transverse arch pressurizing portion. After placing the feet, setting the instep covers to the coupling state allows the feet to be tightly held to the foot contact surfaces to prevent the soles from being displaced from the correct positions.

Effect of the Invention

As described above, wearing the footwear of the present invention allows the transverse arches of the feet to be preferably corrected and stretched.

BRIEF DESCRIPTION OF THE DRAWINGS

FIG. 1(a) and FIG. 1(b) are perspective views of a sandal 1 of an embodiment. FIG. 1(a) illustrates a covering state of an instep cover 3. FIG. 1(b) illustrates an open state of the instep cover 3.

DETAILED DESCRIPTION OF EMBODIMENTS

A description will be given of embodiments of the present invention in accordance with the following embodiments.

Embodiment 1

Figures 1A, 1B:
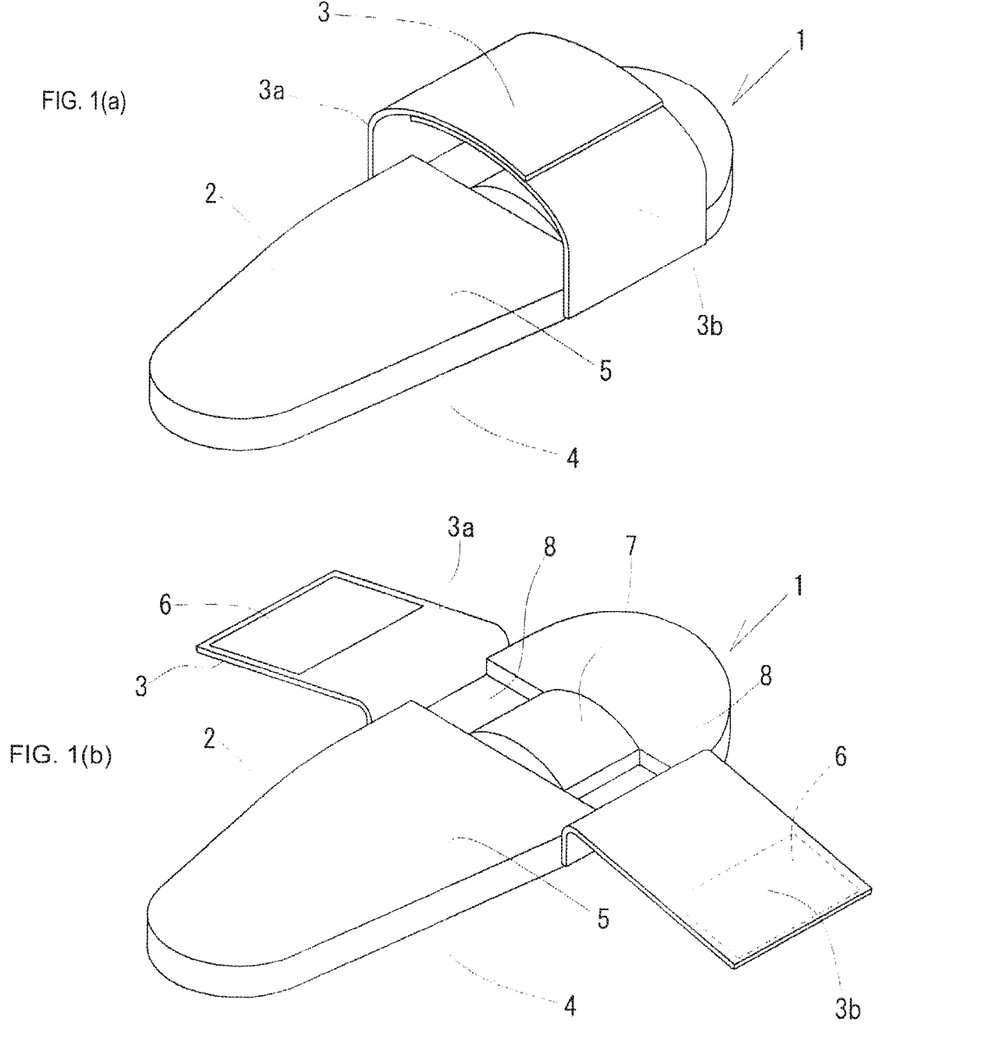

This embodiment applies the present invention to sandals. As illustrated in FIG. 1(a) and FIG. 1(b), a sandal 1 of this embodiment includes a plate-shaped footwear body 2 that forms a ground contact surface 4 and a foot contact surface 5, and an instep cover 3 that covers an instep of a foot.

The instep cover 3 is consisted of a pair of instep cover pieces 3a and 3b fixedly secured to both right and left side edges of the footwear body 2. The instep cover pieces 3a and 3b are made of, for example, a fabric. The instep cover pieces 3a and 3b include hook-and-loop fasteners (coupling means) 6 on their surfaces. The hook-and-loop fasteners 6 mutually couple the instep cover pieces 3a and 3b so as to be removable/mountable. As illustrated in FIG. 1(a), the hook-and-loop fasteners 6 and 6 are joined to mutually couple the instep cover pieces 3a and 3b. Then, the instep cover 3 is in a covering state covering the instep of the foot. As illustrated in FIG. 1(b), the hook-and-loop fasteners 6 and 6 are peeled off to separate the instep cover pieces 3a and 3b. Then, the instep cover 3 can be in an open state where the instep cover pieces 3a and 3b are open to the outside of the footwear body 2. In such an open state, the entire foot contact surface 5 is open upward. This allows a sole to be placed on the foot contact surface 5 accurately and easily.

Figure 2:
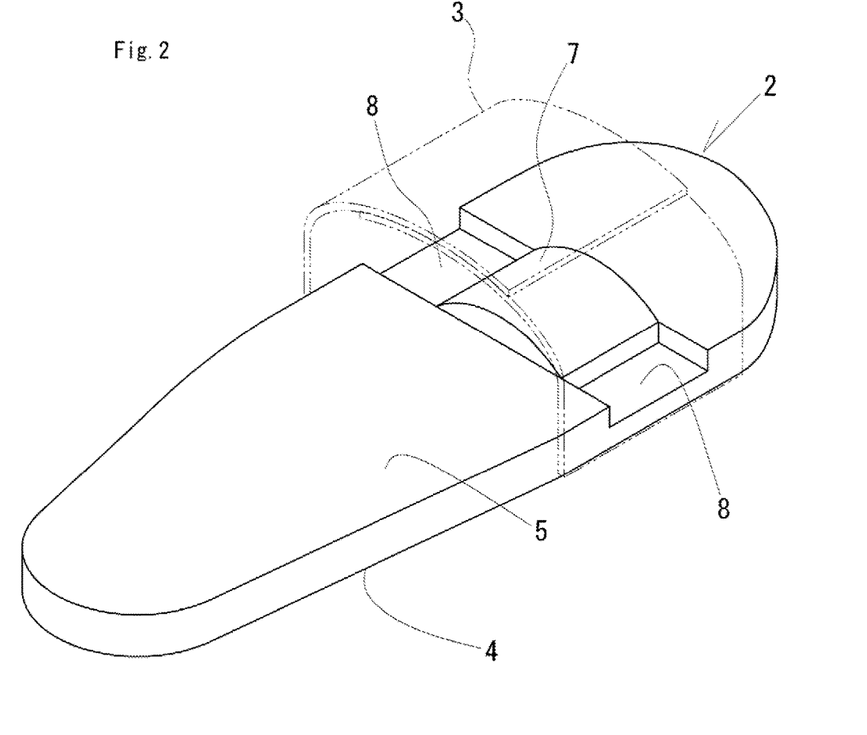
FIG. 2 is a perspective view of a footwear body 2.
Figure 3:
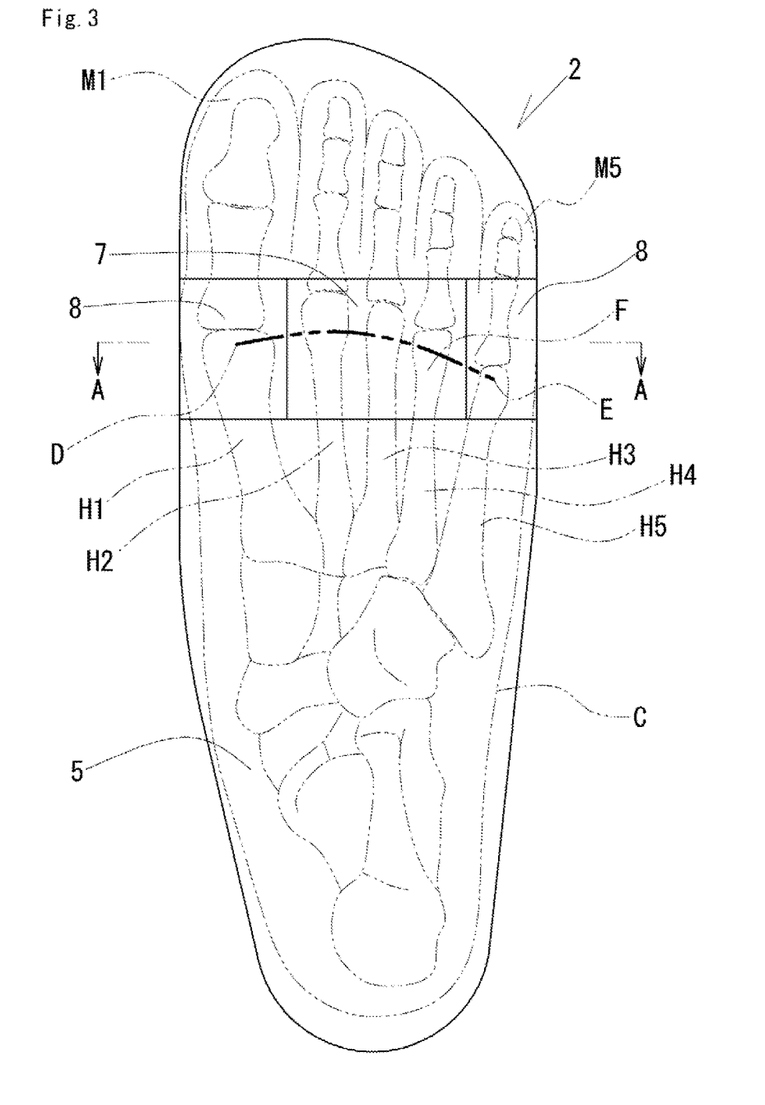
FIG. 3 is a plan view of the footwear body 2.
Figure 4:
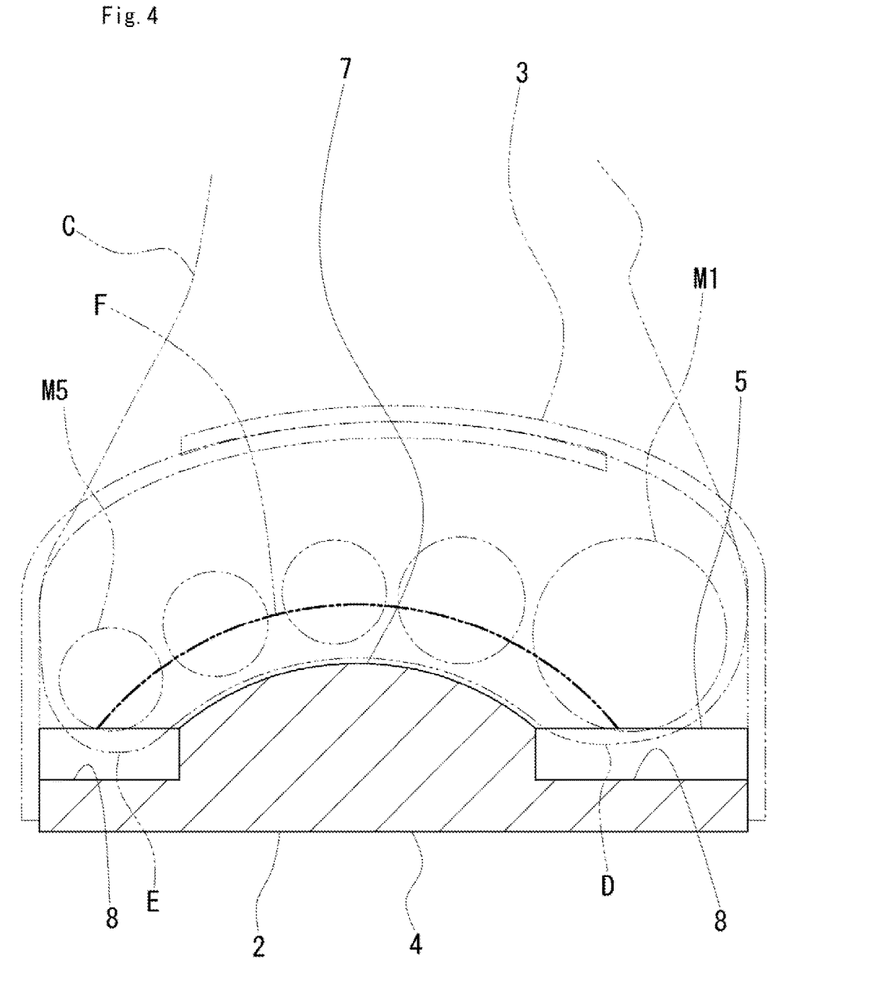
FIG. 4 is a cross-sectional view taken along the line A-A in FIG. 3.

As illustrated in FIGS. 2 to 4, the footwear body 2 is a plate-shaped molded product made of synthetic resin. The footwear body 2 is formed slightly larger than a sole of a wearer. The bottom surface of the footwear body 2 constitutes the ground contact surface 4 in contact with the ground, and the top surface thereof constitutes the foot contact surface 5 in contact with the sole. Here, the ground contact surface 4 is flat while a concavo-convex shape is formed on the foot contact surface 5. Specifically, the concavo-convex shape is formed widthwise at a part of the foot contact surface 5 immediately below a transverse arch F of a foot C. As illustrated in FIGS. 3 and 4, the transverse arch F has the arch structure whose both ends are a thenar eminence D (a joint of a big toe M1) and a hypothenar eminence E (a joint of a little toe M5) and warps upward. The transverse arch F is consisted of muscles and ligaments. To say more strictly, as illustrated in FIG. 3, the transverse arch F has a starting end at a bone head part of a first metatarsal bone H1 (the thenar eminence D). The transverse arch F passes through bone head parts of a second metatarsal bone H2, a third metatarsal bone H3, and a fourth metatarsal bone H4. The transverse arch F has a terminating end at the bone head part of a fifth metatarsal bone H5 (the hypothenar eminence E).

As illustrated in FIGS. 2 to 4, the foot contact surface 5 forms a transverse arch pressurizing portion 7 at a part immediately below between the thenar eminence D and the hypothenar eminence E, namely, a part immediately below the transverse arch F. The widthwise cross-section of the transverse arch pressurizing portion 7 bulges arcwise. The arcwise bulged shape of this transverse arch pressurizing portion 7 in the cross-section forms a curved shape equivalent to the transverse arch F or slightly tighter than the transverse arch F so as to correct and stretch the transverse arch F when placing the feet C. The footwear body 2 is made of a resin material having strong elasticity to prevent large deformation in the cross-sectional shape of the transverse arch pressurizing portion 7 due to the weight of the wearer.

Meanwhile, a right and left pair of escaping portions 8 and 8 are disposed at a part immediately below the thenar eminence D and the hypothenar eminence E of the foot contact surface 5. The escaping portions 8 and 8 are formed so as not to support the thenar eminence D and the hypothenar eminence E. As illustrated in FIG. 4, these escaping portions 8 have flat surfaces formed at positions lower than both side edges of the transverse arch pressurizing portion 7 by around 10 mm. The constitution of the difference in height with the transverse arch pressurizing portion 7 prevents the escaping portions 8 and 8 from being brought in contact with the thenar eminence D and the hypothenar eminence E.

As illustrated in FIG. 4, with such concavo-convex shape of the foot contact surface 5, when placing the feet C on the foot contact surface 5, the thenar eminence D and the hypothenar eminence E are not in contact with the foot contact surface 5. Accordingly, a load usually supported by the thenar eminence D and the hypothenar eminence E is applied to the part placed on the transverse arch pressurizing portion 7.

Thus, with the sandals 1 of this embodiment, the load usually supported by the thenar eminence D and the hypothenar eminence E is applied to the site forming the transverse arch F, between the thenar eminence D and the hypothenar eminence E placed on the transverse arch pressurizing portion 7. In view of this, when standing up straight or walking wearing the sandals 1 of this embodiment, the transverse arch formation site can be strongly pressed from below by the transverse arch pressurizing portion 7 having the bulged shape in the arcwise cross-section. This allows the transverse arch F distorted by wearing the high-heeled footwear or similar footwear to be corrected. Additionally, this allows the muscles that form the transverse arch F to be stretched. Especially, the sandals 1 of this embodiment strongly pressurize the part forming the transverse arch F from below. This is advantageous in that a sufficient effect can be obtained by just wearing the sandals 1 for several minutes to several tens of minutes, eliminating the need for wearing the footwear for a long time.

As illustrated in FIG. 1(b), the sandals 1 of this embodiment places the instep cover 3 in the open state to open the entire foot contact surface 5. This allows the sole to be easily and accurately placed on the transverse arch pressurizing portion 7 and the escaping portion 8. In the state where the sole is accurately placed on the foot contact surface 5, covering the instep of the foot C with the instep cover 3 has an advantage that the positions of the foot contact surface 5 and the sole can be accurately held.

Embodiment 2

Figure 5:
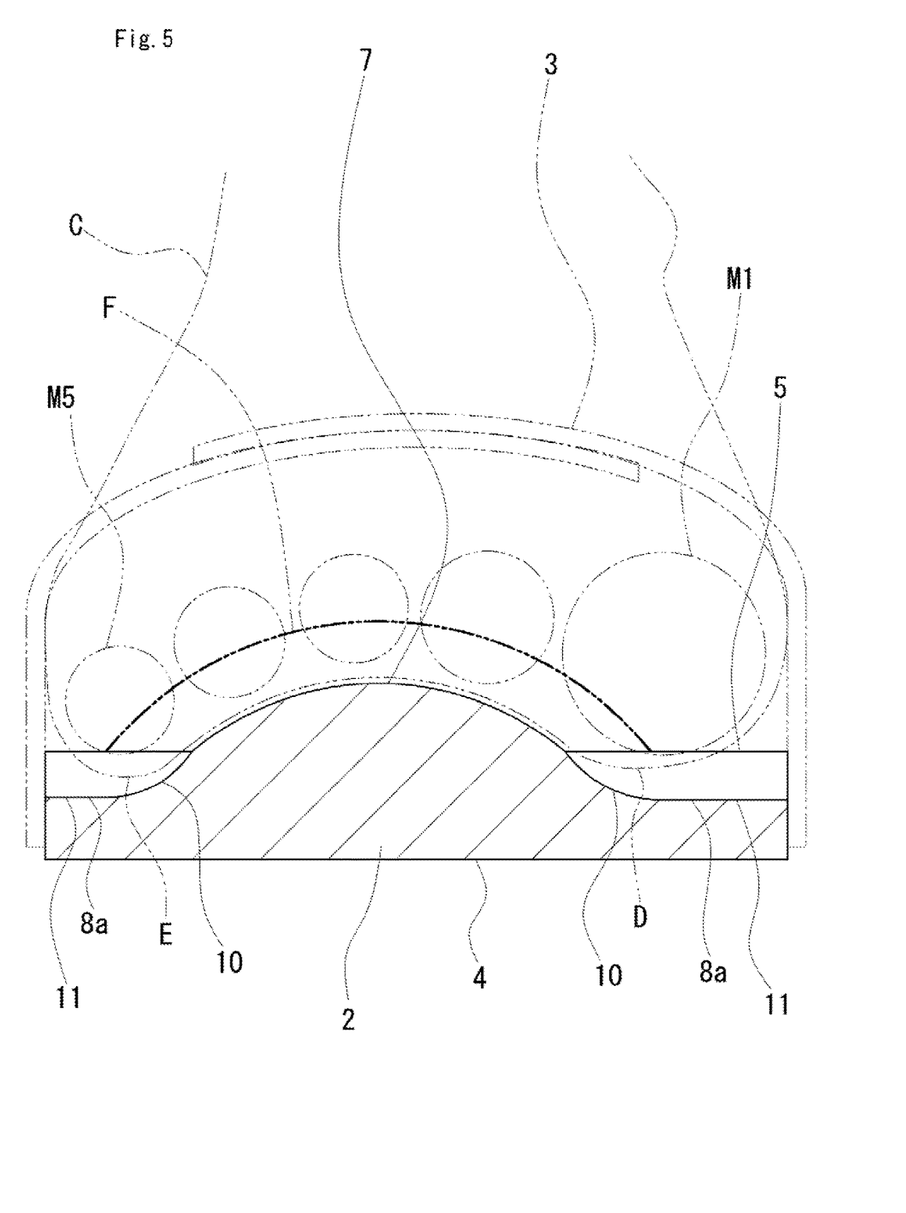
FIG. 5 is a cross-sectional view of the footwear body 2 of Embodiment 2.

In this embodiment, the shape of the escaping portion is changed from that of the embodiment 1. As apparent from the comparison between the cross-sectional views of this embodiment (FIG. 5) and the embodiment 1 (FIG. 4), escaping portions 8a and 8a of this embodiment are consisted of inclined surfaces 10 and flat surfaces 11. The inclined surface 10 is inclined downward from the side edge of the transverse arch pressurizing portion 7 to the outer side. The flat surface 11 is formed on an outer side of this inclined surface 10. Thus, as long as the escaping portion according to the present invention is not in contact with the thenar eminence D and the hypothenar eminence E, the escaping portion may be obliquely recessed. The constitutions of this embodiment and the embodiment 1 are identical except the constitution of the escaping portion 8a. Like reference numerals designate corresponding or identical elements throughout the configurations in common between this embodiment and the embodiment 1, and therefore such elements will not be further elaborated here.

Embodiment 3

Figure 6:
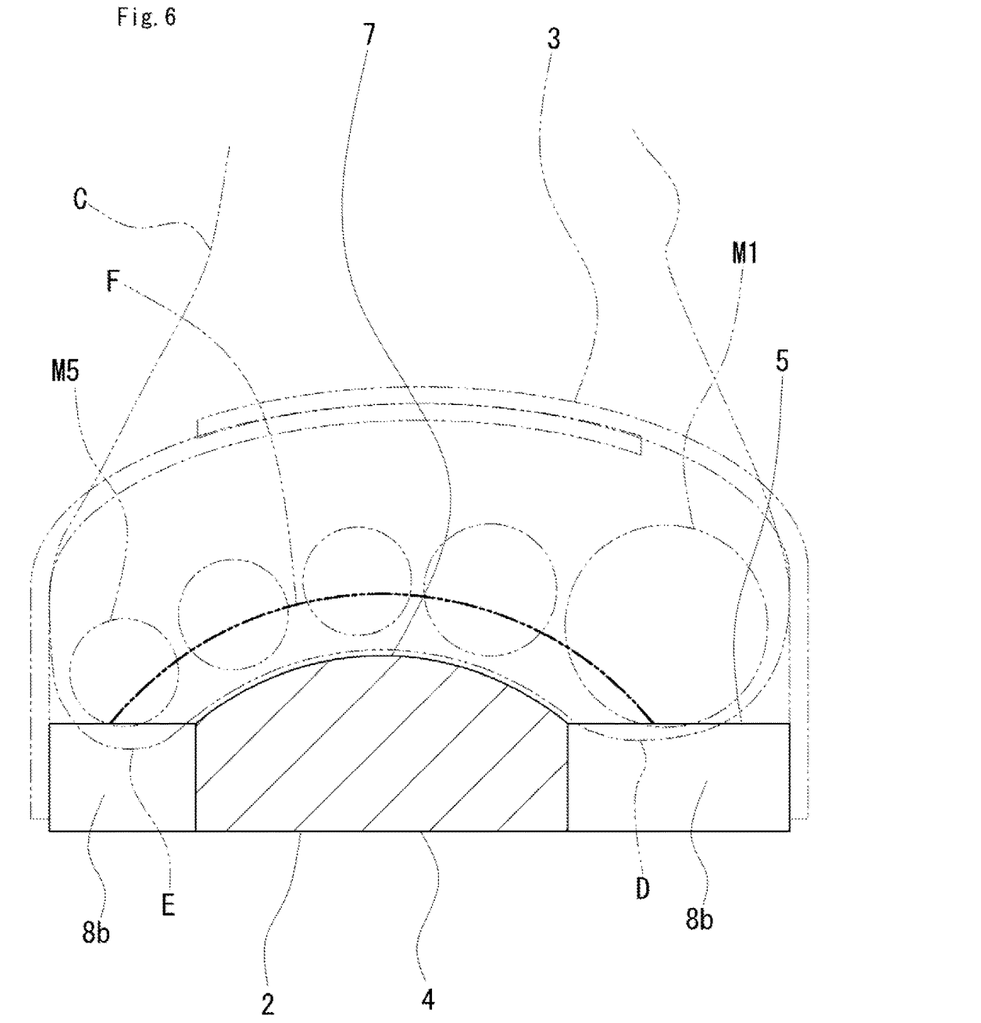
FIG. 6 is a cross-sectional view of the footwear body 2 of Embodiment 3.

In this embodiment, the shape of the escaping portion is changed from that of the embodiment 1. As apparent from the comparison between the cross-sectional views of this embodiment (FIG. 6) and the embodiment 1 (FIG. 4), escaping portions 8b and 8b according to this embodiment are formed by eliminating the parts immediately below the thenar eminence D and the hypothenar eminence E. Thus, the escaping portions according to the present invention are not limited to the recessed portions but can also be constituted of the missing portions. The constitution where the escaping portions are formed of the missing portions can also obtain the effect similar to the constitution of the recessed portions. The constitutions of this embodiment and the embodiment 1 are identical except the constitution of the escaping portion 8b. Like reference numerals designate corresponding or identical elements throughout the configurations in common between this embodiment and the embodiment 1, and therefore such elements will not be further elaborated here.

Embodiment 4

Figure 7:
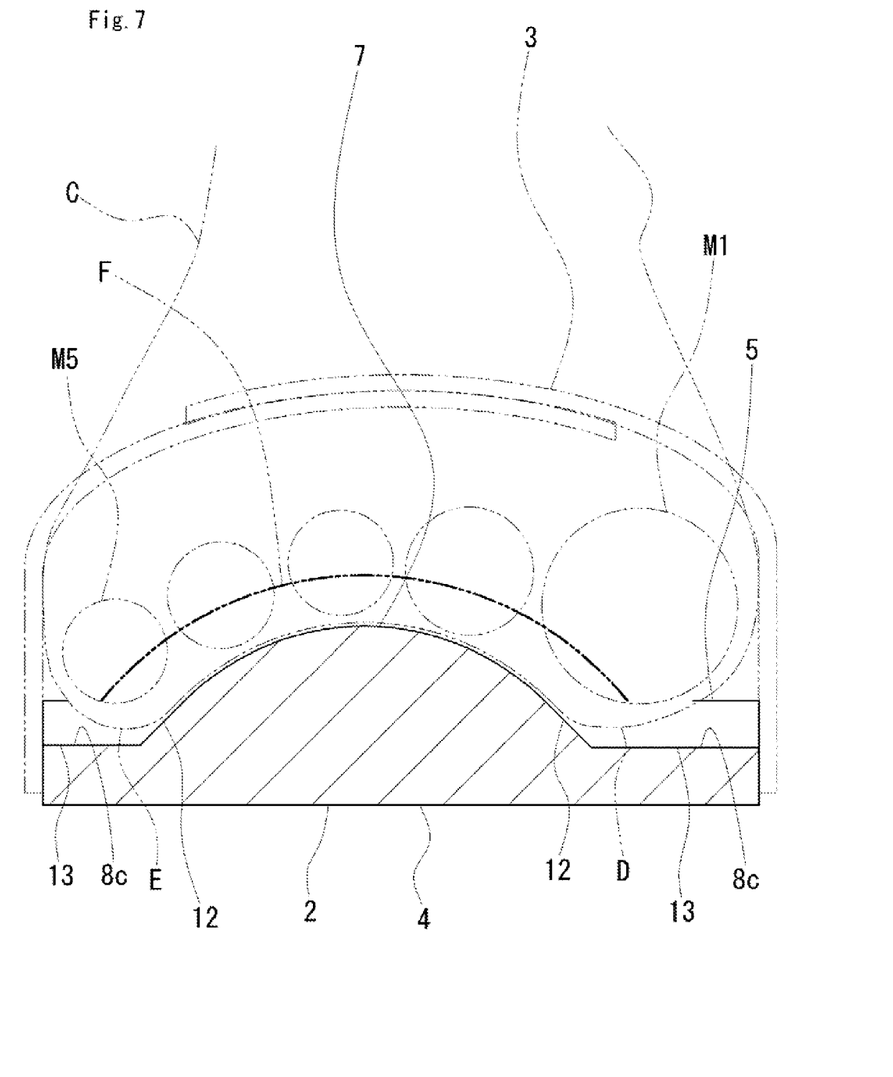
FIG. 7 is a cross-sectional view of the footwear body 2 of Embodiment 4.

In this embodiment, the shape of the escaping portion is changed from that of the embodiment 1. As illustrated in FIG. 7, escaping portions 8c and 8c according to this embodiment are consisted of inclined contacting portions 12 and non-contacting portions 13. The inclined contacting portion 12 is inclined down from the side edge of the transverse arch pressurizing portion 7 to the outer side. The non-contacting portion 13 is formed on an outer side of this inclined contacting portion 12. In this configuration, since the non-contacting portion 13 is formed at the position sufficiently lower than the transverse arch pressurizing portion 7, the non-contacting portion 13 does not come in contact with the thenar eminence D and the hypothenar eminence E. However, the inner portions of the thenar eminence D and the hypothenar eminence E will come in contact with the inclined contacting portions 12, which is continuous with the transverse arch pressurizing portion 7. However, the inclined contacting portion 12 is inclined down to the outside at the acute angle of 45°. Accordingly, even if the inner portions of the thenar eminence D and the hypothenar eminence E are in contact with the inclined contacting portion 12, such contacting parts do not support the body. Thus, as long as the escaping portions according to the present invention are the parts inclined downward to the outer side at the acute angle, even if the escaping portions are brought in contact with the thenar eminence D and the hypothenar eminence E, these contacting portions do not support the body. Accordingly, similar to the other embodiments, the site placed on the transverse arch pressurizing portion 7 is strongly pressurized from below, ensuring correcting and stretching of the transverse arch F. The non-contacting portion 13 according to the embodiment is constituted of the flat surface. However, the non-contacting portion 13 can be an inclined surface or can be a missing portion.

The footwear according to the present invention is not limited to the above embodiments but can be modified in various ways without departing from the scope of the gist of the present invention. For example, the embodiments apply the present invention to the sandals. However, the present invention is also applicable to footwear other than the sandal type. In the above embodiments, the concavo-convex shapes and the missing portions were provided only at the sites corresponding to the transverse arch on the foot contact surface 5. However, as long as the operational effect of the present invention is not lost, the foot contact surface according to the present invention can be formed into the concavo-convex shape or can be eliminated at a site other than that corresponding to the transverse arch.

In the above embodiments, the foot contact surface 5 is formed into a slip surface. However, as long as the operational effect of the present invention is not lost, fine concavo-convex shapes that can provide an anti-slip effect can be formed on the foot contact surface according to the present invention. As long as the operational effect of the present invention is not lost, the concavo-convex shape can also be provided on the ground contact surface 4. Further, in the above-described embodiments 1 to 3, the right and left escaping portions are in approximately symmetrical shapes. However, for example, one side of the escaping portion may be in the shape of the embodiment 1, and the other side of the escaping portion may be in the shape of the escaping portion of the embodiments 2 to 4, such that the right and left escaping portions can be formed into asymmetric shapes.

DESCRIPTION OF REFERENCE NUMERALS

| | |
|---|---|
| 1 | sandal (footwear) |
| 2 | footwear body |
| 3 | instep cover |
| 3a, 3b | instep cover piece |
| 4 | ground contact surface |
| 5 | foot contact surface |
| 6 | hook-and-loop fastener (coupling means) |
| 7 | transverse arch pressurizing portion |
| 8, 8a, 8b, 8c | escaping portion |
| 10 | inclined portion |
| 11 | flat portion |
| 12 | inclined contacting portion |
| 13 | non-contacting portion |
| C | foot |
| D | thenar eminence |
| E | hypothenar eminence |
| F | transverse arch |

The invention claimed is:

1. Footwear to be worn on a human foot, comprising a footwear body having:

a ground contact surface; and
a substantially-flat foot contact surface opposite to the ground contact surface and adapted to support the human foot entirely from toes to a heel, the foot contact surface comprising:
an arch-shaped support, raised above the foot contact surface, adapted to contact and support an area between a thenar eminence and a hypothenar eminence of the human foot when the footwear is worn on the human foot, a cross-section of the supporting portion along a width direction of the foot contact surface, having an arch-shape even when no human foot is placed on the foot contact surface; and
notches located on both sides of the arch-shaped support, respectively, and adapted to be located immediately below the thenar eminence and the hypothenar eminence of the human foot, respectively, when the footwear is worn on the human foot, each notch having an opening in the foot contact surface and a bottom surface located below the foot contact surface, wherein
the foot contact surface adapted to contact, and provide support to, at least the area between the thenar eminence and the hypothenar eminence, the toes, and heel of the human foot, while providing no support to the thenar eminence and the hypothenar eminence of the human foot, when the footwear is worn on the human foot.

2. The footwear according to claim 1, wherein the notches are formed by eliminating parts of the foot contact surface immediately below the thenar eminence and the hypothenar eminence, respectively, to prevent the foot contact surface from being brought in contact with the thenar eminence and the hypothenar eminence.

3. The footwear according to claim 1, wherein at least one of the notches comprises first and second portions, the first portion being inclined downward from a side edge of the supporting portion to an outside at an angle of 45° or more, the second portion being formed outside the inclined contacting portion and adapted to be immediately below the thenar eminence or the hypothenar eminence of the human foot, the second portion being not in contact with the thenar eminence or the hypothenar eminence of the human foot.

4. The footwear according to claim 1, wherein
the footwear is sandal type footwear including the footwear body and an instep cover, the instep cover being adapted to cover an instep of the human foot placed on the foot contact surface,
the instep cover includes a pair of instep cover pieces and coupling means, the respective instep cover pieces being fixedly secured to both lateral portions of the footwear body, the coupling means mutually coupling the pair of instep cover pieces to be removable/mountable, and
the instep cover is changeable between a covering state and an open state, the covering state coupling the pair of instep cover pieces with coupling means to cover the instep of the human foot, the open state mutually separating the pair of instep cover pieces to open the pair of instep cover pieces to an outside.

* * * * *

UNITED STATES PATENT AND TRADEMARK OFFICE
CERTIFICATE OF CORRECTION

PATENT NO.        : 9,717,620 B2
APPLICATION NO.   : 14/836930
DATED             : August 1, 2017
INVENTOR(S)       : Toshiki Ban It is certified that error appears in the above-identified patent and that said Letters Patent is hereby corrected as shown below:

Insert:
--(30) Foreign Application Priority Data
Nov 8, 2013    (JP)    2013-232048--

Signed and Sealed this
Third Day of October, 2017

Joseph Matal
*Performing the Functions and Duties of the*
*Under Secretary of Commerce for Intellectual Property and*
*Director of the United States Patent and Trademark Office*